United States Patent [19]

Balthazor et al.

[11] Patent Number: 4,806,687

[45] Date of Patent: Feb. 21, 1989

[54] CATALYTIC HYDRODESULFURIZATION OF ORTHO-AMINOBENZYLSULFIDES

[75] Inventors: Terry M. Balthazor, University City; Samuel J. Tremont, Manchester, both of Mo.

[73] Assignee: Monsanto Company, St. Louis, Mo.

[21] Appl. No.: 104,593

[22] Filed: Sep. 30, 1987

Related U.S. Application Data

[63] Continuation of Ser. No. 848,323, Apr. 2, 1986, abandoned, which is a continuation of Ser. No. 745,992, Jun. 17, 1985, abandoned, which is a continuation of Ser. No. 496,749, May 20, 1983, abandoned.

[51] Int. Cl.$^4$ .............................................. C07C 85/24
[52] U.S. Cl. ................................... 564/442; 564/443; 564/308
[58] Field of Search ...................... 564/308, 442, 443

[56] References Cited

U.S. PATENT DOCUMENTS

| | | | |
|---|---|---|---|
| 2,793,984 | 5/1957 | Northcott et al. | 196/28 |
| 2,880,171 | 3/1959 | Flinn et al. | 502/220 |
| 3,481,862 | 12/1969 | Davis et al. | 502/220 |
| 3,985,756 | 10/1976 | Gassman et al. | 260/294.8 |
| 4,124,537 | 11/1978 | Gembicki et al. | 252/465 |
| 4,153,578 | 5/1979 | De Thomas et al. | 252/438 |
| 4,172,095 | 10/1979 | Steinman et al. | 260/578 |
| 4,209,464 | 6/1980 | Steinman et al. | 564/442 |
| 4,213,850 | 7/1980 | Reddick et al. | 502/221 |
| 4,404,069 | 9/1983 | Goodin et al. | 564/442 |

OTHER PUBLICATIONS

Tremont et al, J. of Catalysis, vol. 97, pp. 252–260 (1986).
Berkman et al., Catalysis, Reinhold Publishing Corp., New York, 1940, pp. 925–930.
A. C. Cope et al., "Cleavage of Carbon–Sulfur Bonds by Catalytic Hydrodesulfurization", J. Org. Chem., 19, 385 (1954).

Primary Examiner—James H. Reamer
Attorney, Agent, or Firm—Dennis R. Hoerner, Jr.; James W. Williams, Jr.

[57] ABSTRACT

Ortho-alkylanilines are prepared by catalytic hydrodesulfurization of ortho-aminobenzyl sulfides using a cobalt-molybdenum oxide catalyst. For example, 2-methyl-6-trifluoromethylaniline is prepared by catalytic hydrodesulfurization of 3-trifluoromethyl-2-aminobenzyl sulfides. The substituted anilines prepared by the method of this invention are useful as intermediates in the synthesis of compounds shown to have herbicidal activity.

14 Claims, No Drawings

CATALYTIC HYDRODESULFURIZATION OF ORTHO-AMINOBENZYLSULFIDES

This is a continuation of application Ser. No. 848,323, filed Apr. 2, 1986, which is a continuation of application Ser. No. 745,992 filed June 17, 1985, which is a continuation of applicaiton Ser. No. 496,749, filed May 20, 1983, all now abandoned.

BACKGROUND OF THE INVENTION

The present invention relates to the catalytic hydrodesulfurization of ortho-aminobenzyl sulfides to obtain ortho-alkylanilines, and in particular such reactions of 3-trifluoromethyl-2-aminobenzyl sulfides to obtain 2-trifluoromethyl-6-methylaniline.

A number of publications have disclosed methods for the desulfurization of organic sulfur compounds. For example, catalytic hydrogenation at temperatures usually between 623.15° K. (350° C.) and 723.15° K. (450° C.) in the presence of various metals, metallic oxides or sulfides has been used in the petroleum industry to convert the organically combined sulfur in petroleum fractions into hydrogen sulfide, see Berkman et al., Catalysis, Reinhold Publishing Corp., New York, 1940, pp. 925–930. The principle chemical reaction in petroleum fraction hydrodesulfurization is essentially limited to the rupture of simple carbon-sulfur bonds with saturation of olefinic double bonds and aromatic ring structures. In addition, the petroleum industry methods result in a certain amount of denitrification of reactant compounds. The petroleum industry method is unsuitable to promote the class of reactions contemplated by the present invention due to the highly functional substituents present on the orthoaminobenzyl sulfide reactants. In the reactions of the present invention it is desired that the aromatic structure with the substituent groups be retained while cleaving the carbon-sulfur bond to obtain the corresponding substituted aniline. Furthermore, the substituted ortho-aminobenzyl sulfides are generally unstable at the operating temperatures of the petroleum industry method.

Desulfurization by heating with a relatively large amount of Raney nickel has become a useful method in laboratory and small-scale organic synthesis. The principle disadvantages of the Raney nickel method are the large amount of nickel required, commonly three to fifty times the weight of organic reactant, difficulty in isolating products which are adsorbed onto the nickel, and the pyrophoric nature of the reagent. The above mentioned disadvantages make the Raney nickel method unattractive for large scale commercial processes.

While reports of prior work in catalytic hydrodesulfurization of organic substrates outside petroleum processing have been somewhat limited, at least one report in this area taught away from and, as a practical matter, discouraged the low temperature catalytic hydrodesulfurization process of the present invention. See A. C. Cope et al., "Cleavage of Carbon-Sulfur Bonds by Catalytic Hydrodesulfurization", J. Org. Chem.,19, 385 (1954) wherein it was reported that hydrogenation of simple mercaptans such as tert-octyl mercaptan was erratic at 513.15° K. (240° C.) using a commercial cobalt molybdenum catalyst and the inability to hydrogenate a simple sulfide (heptyl sulfide) at 533.15° K. (260° C.) using a commercial cobalt molybdenum catalyst.

It is the overall object of the present invention to provide a process for the catalytic hydrodesulfurization of ortho-aminobenzyl sulfides to obtain ortho-alkylanilines.

It is an object of the present invention to provide a process which is capable of desulfurizing the highly functionalized organic sulfides contemplated by this invention while not substantially effecting substituents present in the organic sulfide reactant.

It is, therefore, another object of the present invention to provide a hydrodesulfurization process capable of operating at mild reaction conditions relative to processes disclosed heretofore.

It is still another object of the present invention to provide a process capable of operating at high concentrations of the organic sulfide reactant to achieve practical payloads.

These and other objects, features, and advantages of the present invention will be evident to one skilled in the art from the following description and examples.

SUMMARY OF THE INVENTION

The present invention embraces the discovery that various ortho-aminobenzyl sulfides can be reductively cleaved by catalytic hydrodesulfurization using a cobalt-molybdenum oxide catalyst in the presence of hydrogen to effect cleavage of the sulfur containing moiety from the benzyl moiety producing the corresponding ortho-alkylaniline. In most cases the hydrodesulfurization reaction proceeds with surprising selectivity, even though the amino substituent would be expected to predispose such organic sulfide reactants to competitive denitrification.

While the process of the present invention can be operated over a broad temperature range, the preferred temperature range is between 423.15° K. (150° C.) and 523.15° K. (250° C.). The rate of reaction can be easily controlled by adjusting the hydrogen pressure within the reactor. While the process can be operated over a broad hydrogen pressure range, the preferred hydrogen gauge pressure is between about 3447.5 kilopascals (500 lbs/in$^2$) and 17237.5 kilopascals (2500 lbs/in$^2$) to obtain practical reaction rates while not overly escalating reactor cost. While the process can operate with essentially any concentration of ortho-aminobenzyl sulfide reactant, as evidenced by Examples 1–3 which were run without solvent, the preferred reactant concentration range is between about 10 and 55 weight percent reactant in suitable solvent.

DETAILED DESCRIPTION OF THE PREFERRED EMBODIMENT

The present invention involves the conversion of ortho-aminobenzyl sulfides, I, to ortho-alkyl anilines, II.

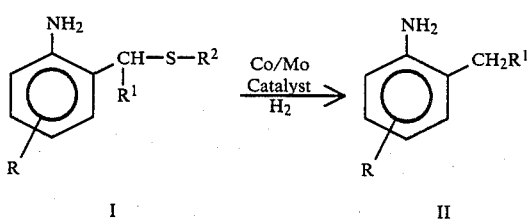

where

R represents alkoxy, alkyl, alkenyl, haloalkyl, halogen, hydroxy or hydrogen $R^1$ represents alkyl, alkenyl or hydrogen $R^2$ represents alkyl, alkenyl, aryl, or hydrogen A reaction of particular interest involves the conversion of 3-trifluoromethyl-2-aminobenzyl sulfides, III, to 2-trifluoromethyl-6-alkylaniline, IV.

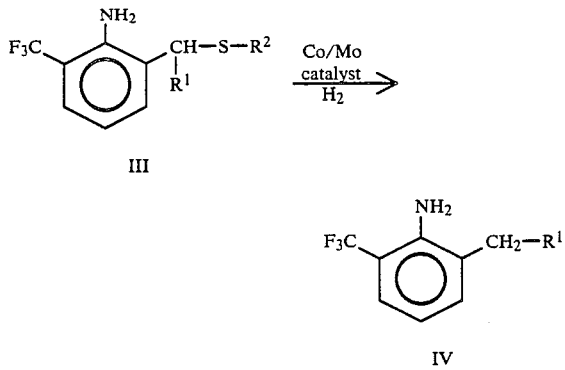

where $R^1$ and $R^2$ have the same meanings as above.

Heretofore, catalytic hydrodesulfurization of aromatic substrates having a trifluoromethyl substituent would have been expected to be unsuccessful since the conventional cobalt-molybdenum on alumina catalyst had been shown to react with the carbon-fluorine bond of benzotrifluoride ($C_6H_5CF_3$) and incorporate the fluorine ion into the catalyst, see U.S. Pat. No. 2,793,984. The present invention embraces the findings that highly functional substituents such as the trifluoromethyl group can be carried through to the product and that in most cases the hydrodesulfurization reaction proceeds with surprising selectivity, even though the amino substituent would be expected to predispose the ortho-aminobenzyl sulfide reactant to competitive denitrification.

As shown above, a wide variety of ortho-aminobenzyl sulfides may be employed in the practice of the present invention. The non-hydrogen, alkyl and other substituent groups represented by R, $R^1$, and $R^2$ can vary over a broad range of number of carbon atoms. As used herein, the term "alkyl" refers to both straight chain and branched chain alkyl radicals ranging between 1 and 10 carbon atoms, preferred are alkyl radicals containing 1 to 6 carbon atoms such as methyl, ethyl, n-propyl, isopropyl, n-butyl, isobutyl, sec-butyl, tert-butyl, n-pentyl, isopentyl, n-hexyl, sec-hexyl, and the like. The term "alkenyl" refers to both straight chain and branched chain alkenyl radicals ranging between 2 and 10 carbon atoms, preferred are alkenyl radicals containing between 3 to 5 carbon atoms such as n-propenyl, isopropenyl, n-butenyl, isobutenyl, n-pentenyl, isopentenyl, and the like. By "alkoxy" is meant a substituent group consisting of an alkyl radical bonded to the base molecule through an oxygen linkage such as methoxy, ethoxy, propoxy, butoxy, etc. The term "aryl" refers to both substituted and unsubstituted aromatic radicals such as benzyl, phenyl, tolyl, xylyl and the like.

Ordinarily, there will be only one of the aforementioned R substituents on a position of the aniline ring, but it is possible to have such substitutents on additional positions and still obtain the desired reaction. The R groups on the ring can be the same or different. The trifluoromethyl group is of particular interest as an R substituent, and methyl, ethyl, methoxy and ethoxy substituents may also be particularly suitable for use. Compounds of particular interest have the R substituent positioned ortho to the amino substituent of the aniline. However, the present process can be effected with the R substituent in the meta or para position.

The $R^1$ group on the benzyl carbon is preferably hydrogen, but alkyl or alkenyl substituents can be used such as methyl, ethyl, ethenyl, etc. In the present process the $R^2$ substituent of the organic sulfide reactant is cleaved and does not appear in the final product. Simple and inexpensive alkyl substituents are preferred. The methylthiomethyl substituent on the aniline ring can be easily prepared by reactions described herein, making the methyl group a simple group to use and, therefore, the preferred choice for the $R^2$ substituent. However, reactants having other $R^2$ groups can be prepared and used if desired. While the $R^1$ and $R^2$ substituents will generally be hydrocarbyl, it should be recognized that non-interfering substituents can be present thereon, and that is also true as to substituents elsewhere in the reactant.

The sulfide starting material for the process of the present invention, represented generally by compounds of type I, may be formed by known sulfilimine rearrangement from the corresponding aniline. For example, an aniline is reacted with dimethyl sulfoxide in the presence of $P_2O_5$ and triethylamine to obtain an aromatic sulfilimine containin an $—N=S—(CH_3)_2$ substituent. The free sulfilimine may be heated or subjected to catalysis to cause sulfilimine rearrangement to an ortho-aminobenzyl sulfide, such as ortho-methylthiomethyl aniline, see Claus et al, Tetrahedron Letters, No. 32, pp 3607–3610, (1968) and Claus et al, Phosphorous and Sulfur, Vol. 1, pp. 11–18 (1976), the disclosures of which are hereby incorporated by reference.

The compounds prouced in the present invention are in general known compounds with known uses, and have been found to have utility as intermediate compounds for the preparation of particular classes of herbicides. Krenzer in U.S. Pat. No. 3,966,811 described compounds of aforementioned types II and IV as useful intermediates for the preparation of acetals of anilinoacetaldehydes which are useful as herbicides. British Patent Application GB No. 2,013,188 and Swiss Patent Nos. 579,348 and 585,191, which have been published, teach anilines including the compounds of types II and IV. The compounds of types II and IV have been found useful in preparation of particularly effective herbicides as described in commonly assigned Belgian Patent No. 887,997 which are particularly effective against perenial weeds such as quackgrass and nutsedge in various crops, particularly corn and soybeans with the acetanilides being particularly exemplified by N-ethoxymethyl-2'-trifluoromethyl-6'-methyl-2-chloroacetanilide.

The compounds are particularly effective as pre-emergence herbicides, although post-emergence activity has also been shown. Compounds of types II and IV can be converted to chloroacetanilides by conventional reaction with chloroacetyl chloride. For example, 2-trifluoromethyl-6-methyl aniline is converted 2'-trifluoromethyl-6'-methyl-2-chloroacetanilide. The chloroacetanilide is then reacted with chloromethylethyl ether in methylene chloride, using benzyl triethylammonium bromide as a phase transfer catalyst to obtain N-ethoxymethyl-2'-trifluoromethyl-6'-methyl-2- chloracetanilide, see U.S. Pat. No. 4,284,564 the disclosure of which is hereby incorporated by reference.

The hydrodesulfurization catalyst involved in one embodiment of the present invention is an unsupported cobalt molybdenum oxide catalyst having the general formula $Co_xMo_yO_z$. Catalyst sulfiding has been shown to increase catalyst activity and can be accomplished by various conventional techniques. While not necessary, presulfiding the cobalt-molybdenum oxide catalyst under an $H_2/H_2S$ mixture as described below is preferred. It should, however, be evident to one skilled in the art that sulfiding of the non-presulfided cobalt-molybdenum oxide catalyst will occur within the reaction mixture and will probably result in an initial low yield of desired product.

The catalyst is easily recycled, stable under storage and reaction conditions and is not pyrophoric. While the process of the present invention can be operated over a broad temperature range, the preferred temperature range is between about 423.15° K. (150° C.) and 523.15° K. (250° C.). It should be understood that the upper limit is determined by the thermal stability of the reactant which will vary with the reactant species selected. The rate of reaction can be easily controlled by adjusting the hydrogen pressure within the reactor. While the process can be operated over a broad hydrogen pressure range, the preferred hydrogen gauge pressure is between 3447.5 kilopascals (500 lbs/in$^2$) and 17237.5 kilopascals (2500 lbs/in$^2$). It should be understood that the process of the present invention can be operated under essentially any hydrogen pressure and should not be considered a critical limitation on the instant invention. Moreover, it is evident to one skilled in the art that lowering the hydrogen operating pressure lowers the rate of reaction and increasing the hydrogen operating pressure increases the rate of reaction. However, higher hydrogen operating pressures result in higher reactor capital cost. Therefore, the principal limitation on hydrogen operating pressures is not one of operability but one of economics. The process can operate with essentially any concentration of ortho-aminobenzyl sulfide reactant as evidenced by Examples 1-3 which were run without solvent. The preferred reactant concentration range is between about 10 and 55 weight percent reactant in suitable solvent. Suitable solvents include, but are not limited to, toluene, chlorobenzene, cyclohexene and tetrahydronaphthalene. It should be evident to those skilled in the art that the particular solvent, optimal temperature and hydrogen pressure will vary with the reactant species.

It is evident to those skilled in the art that there are various ways of synthesizing cobalt-molybdenum oxide catalyst. The following is a suitable method for synthesis of the cobalt-molybdenum oxide catalyst utilized to promote the reactions embodied in the present invention. It should be understood that one skilled in the art may use alternate methods to synthesize or may purchase various commercial cobalt-molybdenum oxide catalysts for use in the hydrodesulfurization process and still be within the scope and spirit of the present invention.

Unsupported catalyst having the formula $Co_1Mo_2O_z$ was prepared as follows: Ammonium molybdate [$(NH_4)_6Mo_7O_{24} \cdot 6H_2O$, 44.03 grams, 0.0356 mole] and cobalt nitrate [$Co(NO_3)_3 \cdot 6H_2O$, 36.29 grams, 0.1246 mole] were separately dissolved in 50 ml of distilled water. The cobalt nitrate solution was added to the ammonium molybdate solution and the resulting mixture was heated to dryness at 343.15° K. (70° C.) with thorough mixing. The dried mixture was then calcined at 373.15° K. (100° C.) for 1 hour and 723.15° K. (450° C.) for 5 hours. The recovered solid weighed about forty-four grams.

The above-described procedure can be used to prepare a cobalt-molybdenum oxide catalyst having essentially any atomic ratio of cobalt to molybdenum by using the proper mole ratio of ammonium molybdate $((NH_4)_6MoO_{24} \cdot 6H_2O)$ and cobalt nitrate $(Co(NO_3)_3 \cdot 6H_2O)$. It is evident to those skilled in the art that cobalt-molybdenum oxide catalysts are operable over a wide range of cobalt to molybdenum ratios. The preferred range for the cobalt to molybdenum ratio is about 1:4 to 4:1.

The catalyst was presulfided as follows: Catalyst prepared as described above was loaded into a 12.7 mm (0.5 inch) inside diameter quartz reactor equipped with a glass frit at the inlet and 6.35 mm (0.25 inch) tube at the outlet. The catalyst was heated at 573.15° K. (300° C.) for 3 hours under a nitrogen flow of $2.22 \times 10^{-6}$ m$^3$/sec (133 cc/min) in order to drive off any water. The reactor was then cooled to 523.15° K. (250° C.) and the nitrogen flow continued. An $H_2/H_2S$ mixture about 10/1 by volume was baffled through the catalyst at about $1.83 \times 10^{-6}$ m$^3$/sec (110 cc/min). The $H_2/H_2S$ flow was continued until $H_2S$ was detected at the outlet of the reactor by exposing the exit gas stream to lead acetate paper. Following sulfurization the catalyst was dark black.

The sulfided, unsupported catalyst is transferred to an autoclave slurry reactor preferably maintained under an oxygen free environment thereby providing a suitable reducing atmosphere while also minimizing passivation of the sulfided cobalt-molybdenum catalyst. Suitable means for maintaining a reducing atmosphere include, but are not limited to, maintaining the reactor under an inert gas blanket such as argon. Reactant material in suitable solvent, if used, is placed in the autoclave reactor. After securing the reactor the pressure is preferably adjusted to about 137.9 kilopascals (20 psig) with hydrogen gas. After heating to 473.15° K. (200° C.) with stirring, the reactor pressure is adjusted to 13790 kilopascals (2000 psig) with hydrogen gas. The slurry reaction is allowed to proceed for about 5 hours. The reactor is now cooled down and gaseous products vented. The liquid is filtered by conventional means and recovered from the catalyst. Product is recovered from the liquid by conventional means such as distillation.

In another embodiment of the present invention, unsupported cobalt-molybdenum oxide catalyst is pressed into pellets. The unsupported catalyst prepared as described above can be presulfided as described above either before or after being pressed into pellets. The pellets can be easily formed on a single punch Stoakes Tablet Machine adjusted to yield a cylindrical pellet 4.76 mm (3/16 inch) in diameter and 4.76 (3/16 inch) long. The average side crush strength is preferably adjusted between 34.475 kilopascals (5 lbs/in$^2$) and 55.16 kilopascals (8 lbs./in$^2$). The catalyst pellets are loaded into a small stainless steel basket mounted to the cooling coil in the interior of the autoclave reactor. The reaction is performed in the same manner as the above-described slurry reaction. The pelletized catalyst is suitable for use in trickle bed or fixed bed reactors.

In yet another embodiment of the present invention, the cobalt-molybdenum catalyst of the present invention can be incorporated onto suitable solid support material. Suitable solid support materials include, but are not limited to, carbon, titanium oxide, magnesium oxide, modified zeolites, and alumina. Incorporation onto solid support materials is accomplished by conventional techniques, for example see Wovel et al, J. Catalysis 68, 453 (1981), the disclosure of which is hereby incorporated by reference.

Supported cobalt-molybdenum oxide catalyst comprising 13% $MoO_3$ and 3% $CoO$ incorporated on carbon support material was prepared as follows: Ammonium molybdate [$(NH_4)_6Mo_7O_{24} \cdot 4H_2O$, 4.78 grams] was dissolved in 25 ml. of warm distilled water. The ammonium molybdate solution was rapidly added to 25.2 grams of Witco Grade 235 carbon that had been previously dried at 393.15° K. (120° C.) under vacuum. Care was taken to evenly mix the aqueous ammonium molybdate solution with the solid carbon support. The resulting impregnated carbon was dried on a hot plate at 353.15° K. (80° C.) for 1 hour. The impregnated carbon was calcined at 383.15° K. (110° C.) for one hour and then 723.15° K. (450° C.) for one hour. Cobalt Nitrate [$Co(NO_3)_2 \cdot 6H_2O$, 3.49 grams] was dissolved in 25 ml of warm water and then added to the molybdenum impregnated carbon. The carbon solid was then dried at 353.15° K. (80° C.) on a hot plate and subsequently calcined at 723.15° K. (450° C.) for 1 hour in air. The final 13% $MoO_3$, 3% $CoO$ on carbon catalyst weighed 27.6 grams.

The following examples are included to better illustrate the practice of the present invention. It should be understood that these examples are included for illustrative purposes only and are not, in any way, intended to limit the scope of the present invention.

EXAMPLE 1

A 4.0 gram sample of Nalcomo 477 catalyst (3.3% CoO and 14.0% $MoO_3$ on $Al_2O_3$ support Sample 78-5995-A, Nalco Chemical Company, Petroleum Division, Chicago, IL) was powdered and presulfided by the above described method. The presulfided catalyst powder was transferred to a stainless steel autoclave reactor under an argon blanket. A 130 mmole (20.0 grams) aliquot of 2-methylthiomethyl aniline was transferred to the autoclave reactor. The reactor was pressurized to 10342.5 kilopascals (1500 lbs/in$^2$) gauge with hydrogen gas. The contents were then stirred and heated to 473.15° K. (200° C.).

After 6 hours, the autoclave reactor was cooled and depressurized. The reactor contents were then washed out with a 300 ml aliquot of dichloromethane. The catalyst was filtered from the liquid contents. The mercaptan by-products were extracted with two 100 ml washings of 10% sodium hydroxide. The organic phase was then dried with magnesium sulfate. The magnesium sulfate was removed by filtration. Distillation yielded the 2-methylaniline product. Product identity was verified by gas chromatography. Conversion was 92% of theoretical.

EXAMPLE 2

A 5.7 gram sample of Nalcomo 477 catalyst was powdered, presulfided and transferred to the stainless steel autoclave reactor as described in Example 1. A 210 mmole (39.0 grams) aliquot of 2-methoxy-6-methylthiomethyl aniline was transferred to the autoclave reactor. The reactor was pressurized to 8963.5 kilopascals (1300 lbs/in$^2$) gauge with hydrogen gas. The contents were then stirred and heated to 473.15° K. (200° C.).

After 5 hours, the autoclave reactor was cooled and depressurized. The reactor contents were washed out with 400 ml of dichloromethane and the mixture filtered to yield a light yellow solution. Subsequent drying and filtering gave an amber liquid. Distillation yielded the 2-methoxy-6-methylaniline product. Product identity was verified by gas chromatography. Conversion was 95% of theoretical.

EXAMPLE 3

A 4.0 gram sample of Nalcomo 477 catalyst was powdered, sulfided and transferred to a stainless steel autoclave reactor as described in Example 1. A 100 mmole (20.0 grams) aliquot of 2-chloro-6-methylthiomethyl aniline was transferred to the autoclave reactor. The reactor was then pressurized to 10342.5 kilopascals (1500 lbs/in$^2$) gauge with hydrogen gas. The contents were then stirred and heated to 473.15° K. (200° C.).

After 5 hours, the reactor was cooled, depressurized and allowed to stand overnight. The reaction mixture was washed out with dichloromethane and then extracted with 10% sodium hydroxide. Subsequent drying and filtering yielded a brown liquid. Distillation yielded the 2-chloro-6-methyl aniline product. Product identity was verified by gas chromatography. Conversion was 87% of theoretical.

EXAMPLE 4

A 4.0 gram sample of an unsupported cobalt-molybdenum oxide catalyst powder having a Co:Mo atomic ratio of 1:1 was purchased ($CoMoO_4 \cdot H_2O$, Reagent Grade RA 304, City Chemical Corp., New York, N.Y.) and presulfided according to the above described procedure. The presulfided catalyst powder was transferred to a 300 ml stainless steel autoclave reactor under an argon blanket. A 150 gram aliquot of 25 wt. percent solution of 2-trifluoromethyl-6-methylthiomethyl aniline in toluene was charged into the autoclave reactor. The reactor contents were stirred and heated to 473.15° K. (200° C.) under a hydrogoen gauge pressure of 137.9 kilopascals (20 lbs/in$^2$). The reactor was then pressurized to 13790 kilopascals (2000 lbs/in$^2$) gauge with hydrogen gas.

After 5 hours, the reactor was cooled and depressurized. The reactor contents were recovered and the 2-trifluoromethyl-6-methylaniline product isolated as described in the previous examples. Product identity was verified by gas chromatography. Conversion was 96% of theoretical.

EXAMPLE 5

A 4.0 gram sample of an unsupported cobalt-molybdenum oxide catalyst powder having a Co:Mo atomic ratio of 1:4 was prepared and presulfided according to the above described procedures. The presulfided catalyst poweder was transferred to a 300 ml stainless steel autoclave reactor under an argon blanket. A 150 gram aliquot of 25 wt. percent solution of 2-trifluoromethyl-6-methylthiomethylaniiline in toluene was charged into the autoclave reactor. The reactor contents were stirred and heated to 473.15° K. (200° C.) under a hydrogen gauge pressure of 137.9 kilopascals (20 lbs/in$^2$). The reactor was then pressurized to 13790 kilopascals (2000 lbs/in$^2$) gauge with hydrogen gas.

After 7 hours, the reactor was cooled and depressurized. The reactor contents were recovered and the 2-rrifluoromethyl-6-methylaniline product isolated. Product identity was verified by gas chromatography. Conversion was 70% of theoretical.

EXAMPLE 6

An identical experiment was conducted as described in Example 5 with the exception that the cobalt-molybdenum catalyst prpared had a Co:Mo atomic ratio of 1:2.

After 6 hours, the reactor was cooled and depressurized. The reactor contents were recovered and the 2-trifluoromethyl-6-methylaniline product isolated. Product identity was verified by gas chromatography. Conversion was 54% of theoretical.

EXAMPLE 7

An identical experiment was conducted as described in Example 5 with the exception that the cobalt-molybdenum catalyst prepared had a Co:Mo atomic ratio of 2:1.

After 7 hours, the reactor was cooled and depressurized. The reactor contents were recovered and the 2-trifluoromethyl-6-methylaniline product isolated. Product identity was verified by gas chromatography. Conversion was 80% of theoretical.

EXAMPLE 8

An identical experiment was conducted as described in Example 5 with the exception that the cobalt-molybdenum catalyst prepared had a Co:Mo atomic ratio of 4:1.

After 4 hours, the reactor was cooled and depressurized. The reactor contents were recovered and the 2-trifluoromethyl-6-methylaniline product isolated. Product identity was verified by gas chromatography. Conversion was 95% of theoretical.

EXAMPLE 9

An identical experiment was conducted as described in Example 5 with the exception that the cobalt-molybdenum oxide catalyst prepared had a Co:Mo atomic ratio of 1:1 and was supported on carbon as described in the above described procedure.

After 6 hours, the reactor was cooled and depressurized. The reactor contents were recovered and the 2-trifluoromethyl-6-methylaniline product isolated. Product identity was verified by gas chromatography. Conversion was 95% of theoretical.

EXAMPLE 10

An 8.0 gram sample of an unsupported cobalt-molybdenum oxide powder having a Co:Mo atomic ratio of 1:1 was prepared and presulfided according to the above described procedures. The presulfided catalyst powder was transferred to a 300 ml stainless steel autoclave reactor under an argon blanket. A 180 gram aliquot of a 50 weight percent solution of 2-trifluoromethyl-6-methylthiomethylaniline in toluene was charged into the autoclave reactor. The reactor contents were stirred and heated to 513.15° K. (240° C.) under a hydrogen gauge pressure of 137.9 kilopascals (20 lbs/in²). The reactor was then pressurized to 13790 kilopascals (2000 lbs/in²) gauge with hydrogen gas.

After 2.58 hours, the reactor was cooled and depressurized. The reactor contents were recovered and the 2-trifluoromethyl-6-methylaniline product isolated as described in the previous examples. Product identity was verified by gas chromatography. Conversion was 91% of theoretical.

EXAMPLE 11

A 1.0 gram sample of cobalt-molybdenum oxide catalyst as described in Example 4 was presulfided according to the above described procedures. The presulfifed catalyst powder was transferred to a 100 ml stainless steel bomb under an argon blanket. A 54 gram aliquot of a 7.4 weight percent solution of 2-trifluoromethyl-6-methylthiomethylaniline in tetralin was charged into the stainless steel bomb. The bomb was initially pressurized to 689.5 kilopascals gauge (100 lbs/in²) with hydrogen gas. Thereafter, the bomb contents were stirred and heated to 429.15° K. (156° C.) The hydrogen gauge pressure was then increased to 965.3 kilopascals (140 lbs/in²).

After 41 hours, the bomb was cooled and depressurized. The bomb contents were recovered and the 2-trifluoromethyl-6-methylaniline product isolated as described in the previous examples. Product identity was verified by gas chromatography. Conversion was 38% of theoretical.

We claim:

1. A process for preparing 2-trifluoromethyl-6-alkylanilines which comprises reacting a 3-trifluoromethyl-2-aminobenzyl sulfide with hydrogen in the presence of an unsupported cobalt molybdenum oxide catalyst at a temperature and hydrogen pressure sufficient to effect cleavage of the sulfur-containing moiety from the benzyl moiety producing a 2-trifluoromethyl-6-alkylaniline.

2. A process of claim 1 in which the reaction is represented by:

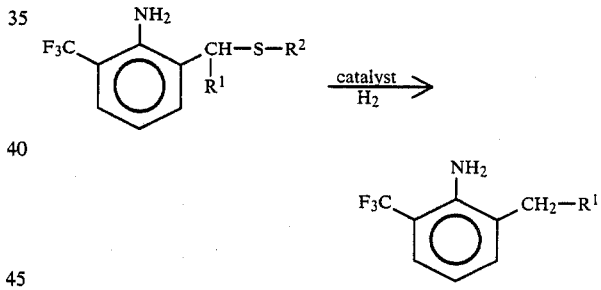

where
$R^1$ represents alkyl, alkenyl, or hydrogen
$R^2$ represents alkyl, alkenyl, aryl, or hydrogen.

3. A process of claim 1 in which the reaction is carried out at a temperature between 423,15° K. (150° C.) and 523.15° K. (250° C.) and a hydrogen gauge pressure between 3447.5 kilopascals (500 lbs/ins²) and 17237.5 kilopascals (2500 lbs/in²).

4. A process of claim 1 further comprising the use of a solvent selected from the group consisting of chlorobenzene, cyclohexene, tetrahydronaphthalene and toluene.

5. A process of claim 1 in which the catalyst is presulfieded.

6. A process of claim 1 in which 3-trifluoromethylsulfide is converted to a 2-trifluoromethyl-6-methylaniline.

7. A process of claim 1 in which the catalyst contains a cobalt to molydenum ratio between 1:4 and 4:1.

8. A process for preparing 2-trifluoromethyl-6-alkylanilines which comprises reacting a 3-trifluoromethyl-2-aminobenzyl sulfide with hydrogen in the presence of a carbon supported cobalt molybdenum oxide catalyst at a temperature and hydrogen pressure sufficient to effect cleavage of the sulfur-containing moiety from the benzyl moiety producing a 2-trifluoromethyl-6-alkylaniline.

9. A process of claim 5 in which the reaction is represented by:

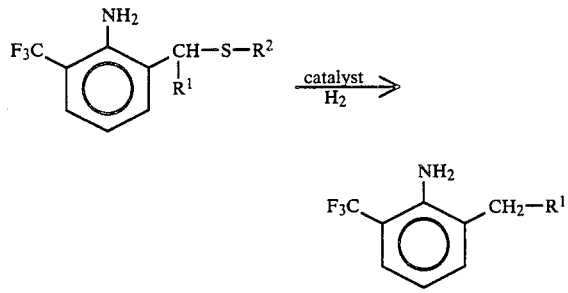

where
R¹ represents alkyl, alkenyl, or hydrogen
R² represents alkyl, alkenyl, aryl, or hydrogen.

10. A process of claim 5 in which the reaction is carried out at a temperature between 423.15° K. (150° C.) and 523.15° K. (250° C.) and a hydrogen gauge pressure between 3447.5 kipopascals (500 lbs/in²) and 7237.5 kipopascals (2500 lbs/in²).

11. A process of claim 5 further comprises the use of a solvent selected from the group consisting of chlorobenzene, cyclohexene, tetrahydronapthalene and tolune.

12. A process of claim 5 in which the catalyst is pre-sulfided.

13. A process of claim 5 in which 3-trifluoromethyl-2-aminobenzylmethylsulfide is converted to a 2-trifluoromethyl-6-methylaniline.

14. A process of claim 5 in which the catalyst contains a cobalt to molybdenum ratio between 1:4 and 4:1.

* * * * *